United States Patent [19]
Le et al.

[11] Patent Number: 5,801,954
[45] Date of Patent: Sep. 1, 1998

[54] PROCESS FOR DESIGNING AND CHECKING A MASK LAYOUT

[75] Inventors: Chin Aik Le; Christophe Pierrat, both of Boise, Id.

[73] Assignee: Micron Technology, Inc., Boise, Id.

[21] Appl. No.: 637,307

[22] Filed: Apr. 24, 1996

[51] Int. Cl.⁶ .................................................. G06F 17/50
[52] U.S. Cl. .......................... 364/488; 382/144; 430/5
[58] Field of Search ................................. 364/488, 489, 364/490, 491; 382/144; 430/5

[56] References Cited

U.S. PATENT DOCUMENTS

| | | | |
|---|---|---|---|
| 5,046,109 | 9/1991 | Fuijmori et al. | 382/8 |
| 5,308,722 | 5/1994 | Nistler | 430/5 |
| 5,326,659 | 7/1994 | Liu et al. | 430/5 |
| 5,376,483 | 12/1994 | Rolfson | 430/5 |
| 5,379,348 | 1/1995 | Watanabe et al. | 382/8 |
| 5,441,834 | 8/1995 | Takekuma et al. | 430/5 |
| 5,442,714 | 8/1995 | Iguchi | 382/144 |
| 5,481,624 | 1/1996 | Kamon | 382/144 |
| 5,572,598 | 11/1996 | Wihl et al. | 382/144 |
| 5,686,208 | 11/1997 | Le et al. | 430/5 |
| 5,695,896 | 12/1997 | Pierrat | 430/5 |

FOREIGN PATENT DOCUMENTS

| | | | |
|---|---|---|---|
| 2-140743 | 5/1990 | Japan | G03F 1/08 |

OTHER PUBLICATIONS

"Wavefront Engineering for Photolithography" by Marc D. Levenson, Physics Today, Jul. 1993. no page numbers.
"Lithography's Leading Edge, Part 1: Phase–shift Technology" by Pieter Burggraaf, Senior Editor, Semiconductor International, Feb. 1992., no page numbers.

*Primary Examiner*—Emanuel Todd Voeltz
*Assistant Examiner*—Leigh Marie Garbowski
*Attorney, Agent, or Firm*—Arnold, White & Durkee

[57] ABSTRACT

A process for designing and checking a mask layout is provided. A mask layout is generated from a binary mask layout design. An aerial image of the mask layout is then calculated using simulation software. The simulated aerial image is then compared to the binary mask layout design and modifications are made to the mask layout if necessary.

6 Claims, 4 Drawing Sheets

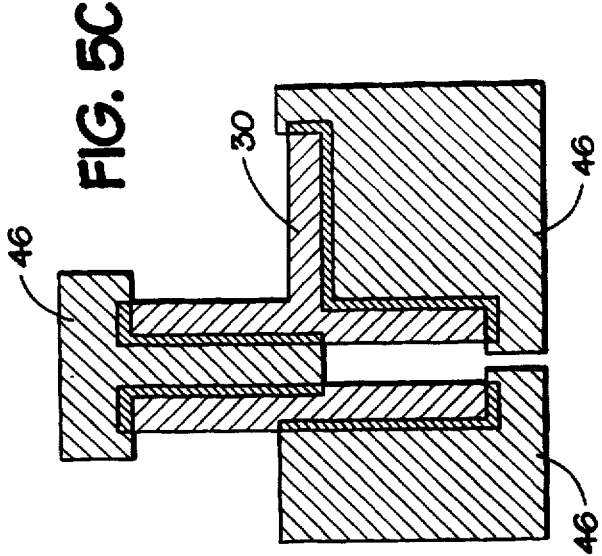
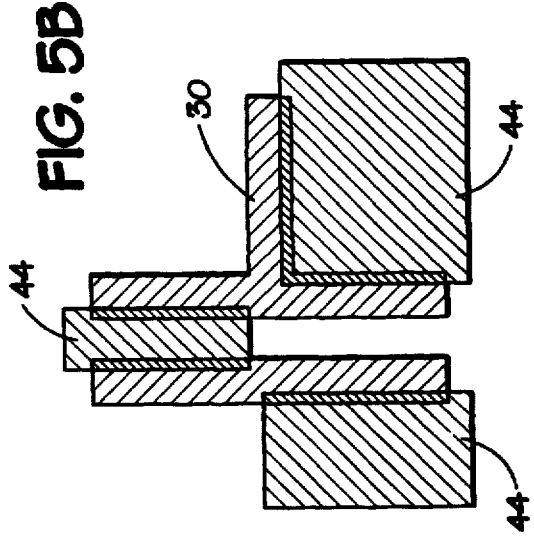
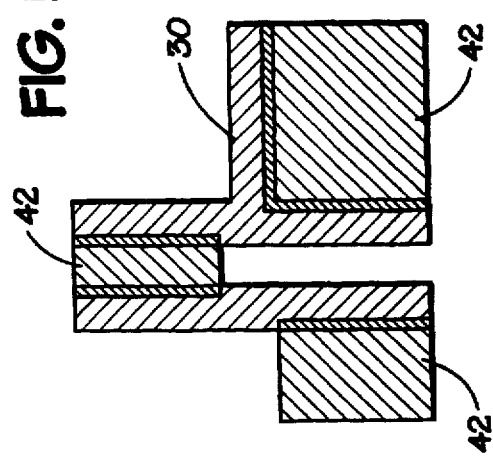
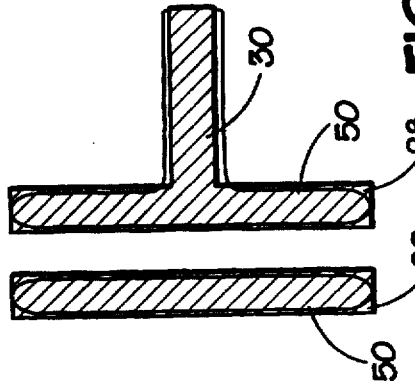
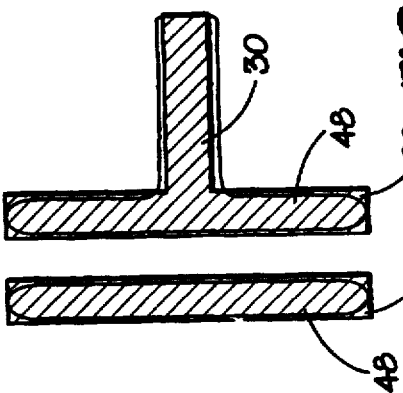

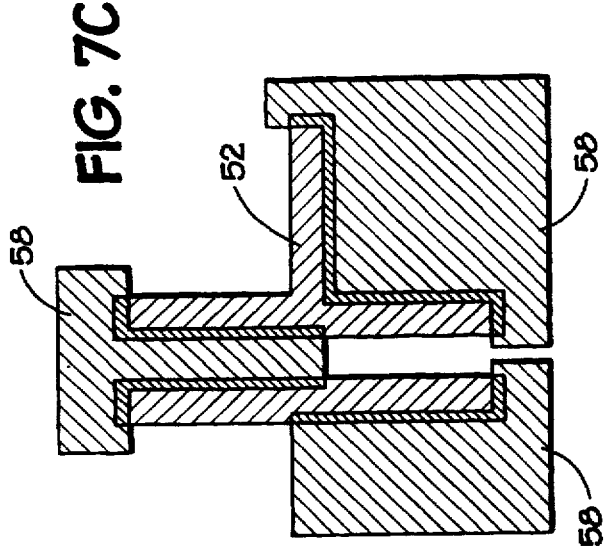
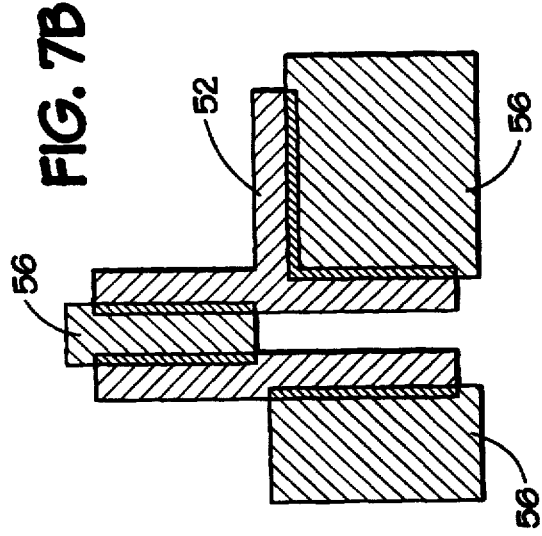
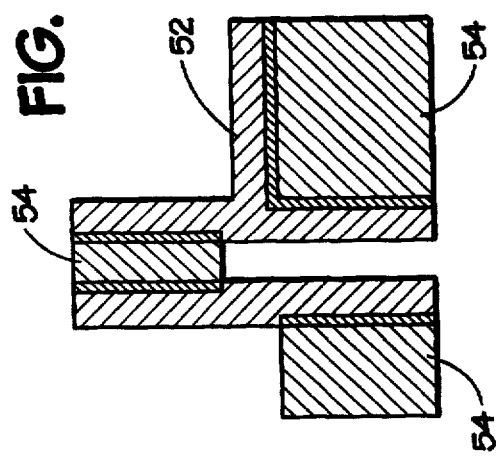
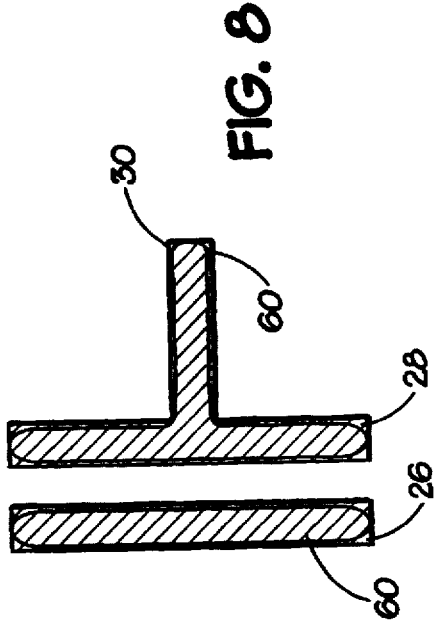

PROCESS FOR DESIGNING AND CHECKING A MASK LAYOUT

BACKGROUND OF THE INVENTION

This invention was made with government support under Contract No. MDA 972-92-C-0054 awarded by Advanced Research Projects Agency (ARPA). The government has certain rights in this invention.

The present invention relates to processes for creating photomasks or reticles used in the fabrication of semiconductor devices. More particularly, the present invention relates to processes for generating and checking the patterns used to fabricate masks.

Advances in capacity in semiconductor chips have generally been the result of decreases in the size of the features on the chip. The lateral dimensions of features are generally defined by photolithographic techniques in which a detailed pattern is transferred to a photoresist by shining light through a mask or reticle.

In recent years, phase shifting masks have been developed to improve photolithographic processes. Phase shifting masks increase image contrast and resolution without reducing wave length or increasing numerical aperture. These masks also improve depth of focus and process latitude for a given feature size.

With phase shift photolithography, the interference of light rays is used to overcome the problems of diffraction and improve the resolution and depth of optical images projected onto a target. With this technology, the phase of the exposure light at the target is controlled such that adjacent bright areas are preferably formed 180 degrees out of phase with each other. Dark regions are thus produced between the bright areas by destructive interference even when diffraction would otherwise cause these areas to be lit. This technique improves total resolution at the target.

In general, a phase shifting mask is constructed with a repetitive pattern formed of three distinct layers of material. An opaque layer provides areas that allow no light transmission. A first transparent layer provides areas which allow close to 100% of the light to pass through. A transparent phase shifting layer provides areas which allow close to 100% of the light to pass through but phase shifted 180 degrees from the light passing through the first transparent layer. The first transparent layer and the phase shifting layer are positioned such that light rays diffracted through each area are cancelled out in a darkened area between them. This creates a pattern of dark and bright areas which can be used to clearly delineate features of a pattern defined by the opaque layer on the semiconductor wafer. Another method of constructing a phase shifting mask utilizes a semitransparent layer to cause the phase shift.

One process for fabricating phase shifting masks is disclosed in U.S. Pat. No. 5,308,722 which uses a voting technique to fabricate a defect-free printing mask. The disclosed process includes forming an opaque layer on a major surface of a transparent substrate, patterning the opaque layer to expose portions of the underlying transparent substrate, forming a phase shifting mask layer to expose the portions of the underlying transparent substrate, phase-etching partway into the exposed portions of the transparent substrate by an amount equivalent to a preselected phase shift angle, and voting the phase shifting mask layer to accomplish the phase-etching in a series of steps, each equal to the phase shift angle, until a full 180° phase shift is accomplished. The number of phase-etching steps claimed in the patent is from three to five.

Other processes of fabricating phase shifting masks are disclosed in Japanese Patent Application No. 63-295350. This application discloses processes in which a transparent film is formed over a portion of a mask to create a phase shift as well as the etching of phase shifting channels into the mask substrate.

One of the problems associated with the fabrication of phase shifting masks is the lack of tools available to check the layout after the phase shifting layers have been generated. Those layers, combined with the chrome layer can be very different from what is actually going to print on the wafer.

Another method that has been developed to produce masks for use in the fabrication of semiconductors containing small features is optical proximity effect correction ("OPC"). In this method, changes are made to the binary mask layout so that it will print more clearly. Because of the limited resolution of the current photolithographic tools (i.e., steppers), the patterns defined on the photomask are transferred into the resist on the wafer with some distortions referred to as optical proximity effects. The main consequences in term of line width control are: corner rounding, difference between isolated and semi-isolated or dense patterns, lack of CD linearity where small features print even smaller than their expected size compared to large features and line end shortening where the length of a line having a small line width becomes smaller than its expected size.

Moreover, optical proximity effects are convoluted with subsequent processing step distortions like resist processing, dry etch and wet etch proximity effects. In order to achieve a sufficient line width control at the wafer level, the mask designs are corrected for proximity effects, namely re-entrant and outside serifs are used to correct rounding and the edges of the patterns are moved to correct line width errors.

One of the problems associated with OPC is the lack of an efficient method for checking the design to determine if it will create the desired image since the mask layout design and the printed image are sometimes quite different.

Accordingly, it would be a significant advancement in the art to provide a process for checking a mask layout to see if it will produce the desired image which is simple to perform so that changes can be made if necessary. Such a process is disclosed and claimed herein.

SUMMARY OF THE INVENTION

The present invention provides a novel process for designing and checking mask layouts used in the fabrication of semiconductor devices. In a preferred embodiment, the process of the present invention is used to check the layout for a phase shifting mask. A binary mask layout design is obtained and a phase shifting mask layout is generated using a conventional software program. Aerial image simulation software is then used to generate an aerial image of the simulated wafer image corresponding to the phase shifting mask layout. This simulated wafer image is then compared to the binary mask layout utilizing a conventional design rule checker software program.

The simulated wafer image is calculated at both best focus and best focus ± a focus margin. If the simulated wafer images correspond to the binary mask layout within predetermined parameters, the phase shifting mask layout is passed to production. If the simulated wafer images differ from the binary mask layout by more than a predetermined amount, the phase shifting mask layout is modified. This can be accomplished by modifying the phase shifting layers and/or the line width of the chrome layer. Simulated wafer images are again calculated using aerial image simulation software and the resulting images are compared to the binary mask layout. This process is repeated until the simulated wafer images correspond to the binary mask layout within predetermined design rules.

The process of the present invention can also be used to check the designs of mask layouts generated using optical proximity effect correction ("OPC") techniques. After a mask layout is generated, a simulated wafer image is calculated using the aerial image simulation software at both best focus and best focus ± a focus margin. These images are then compared to the original binary mask layout to see if the designs correlate within predetermined parameters. If they do not, changes are made to the mask layout and the design is again checked.

BRIEF DESCRIPTION OF THE DRAWINGS

FIGS. 5A to 5C are schematic illustrations of a modified phase shifting mask design corresponding to the binary mask layout of FIG. 2.

FIGS. 6A and 6B are schematic illustrations of simulated wafer images superimposed on the binary mask layout of FIG. 2.

FIGS. 7A to 7C are schematic illustrations of a modified phase shifting mask design corresponding to the binary mask layout of FIG. 2 superimposed on a binary mask layout in which the horizontal line has been narrowed from that illustrated in FIG. 2.

FIG. 8 is a schematic illustration of a simulated wafer image superimposed on the binary layout of FIG. 2.

DETAILED DESCRIPTION OF THE INVENTION

The present invention provides a novel process for designing and checking a mask layout used in fabricating semiconductor devices. The invention is best understood by reference to the accompanying drawings in which like parts are designated with like numerals.

Figure 1:
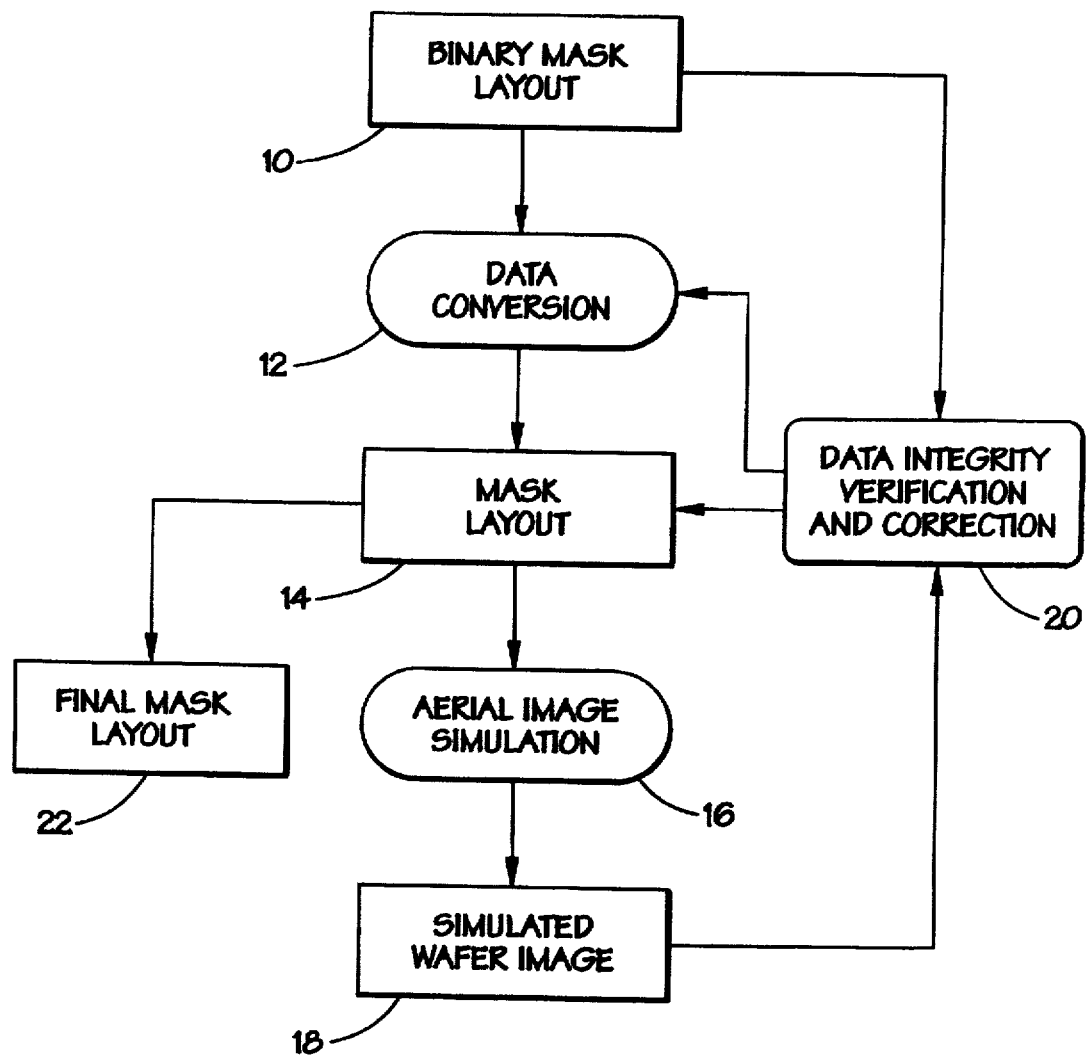
FIG. 1 is a flow chart illustrating a preferred embodiment of the process of the present invention.

Referring first to FIG. 1, a flow chart generally illustrates the process of the present invention. The process begins with a binary mask layout 10. The data from the binary mask layout is then converted by a design program 12 which converts the data to generate a mask layout 14. The process of the present invention can be used with various different design techniques. For example, in a preferred embodiment the design program 12 generates a phase shifting mask layout. In a second preferred embodiment, the design program 12 comprises an optical proximity effect correction program. In a third preferred embodiment, the design program 12 comprises a combination of a phase shift mask layout program and an optical proximity effect correction program.

Many different types of design programs are currently available and known to those skilled in the art. Examples of optical proximity effect correction programs include OPTI-MASK by Vector Technologies of Boston, Mass., OPRX by TVT of Santa Barbara, Calif., and PROXIMA by Precim of Portland, Oreg.

After mask layout 14 is generated, the process of the present invention provides a method of checking that layout to see if it will produce a pattern on a wafer corresponding to the binary mask layout. Data from mask layout 14 is processed by an aerial image simulation program 16 to generate a simulated wafer image 18. In the preferred embodiment, the simulated wafer image is calculated at both best focus and best focus ± a focus margin.

Examples of simulation software that can be used to perform the aerial image simulation include FAIM by Vector Technologies of Boston, Mass., SPLAT by the University of Berkeley, Calif. and PROLITH by Finle Technologies of Plano, Tex.

The simulated wafer image data is then fed to a design rule checker or data integrity verification and correction program 20 where it is compared to the data comprising the original binary mask layout. If the simulated wafer image correlates with the binary mask layout within predetermined parameters or design rules, mask layout 14 is designated as the final mask layout 22. However, if the simulated wafer image 18 differs at either best focus or best focus ± a focus margin from the binary mask layout by more than the design rules, this information is fed back to the design program 12 and a modified mask layout is generated. The modified mask layout is then run through the aerial image simulation software and the images 18 are again compared to the binary mask layout 10. This process is repeated until the simulated wafer images correlate with the binary mask layout within the design rules.

Various different types of design rule checker programs can be used to perform the data integrity verification and correction analysis. Examples of suitable software include CATS by Transcription Enterprises Limited of Los Gatos, Calif., iv Verify by Cadence System Inc. of San Jose, Calif., CheckMate by Mentor Graphics, Wilsonville, Oreg. and VeriCheck by Integrated Silicon System of Research Triangle Park, N.C.

Figure 2:
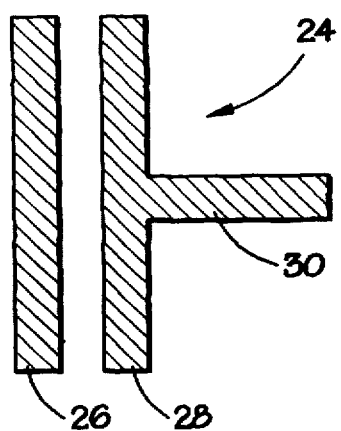
FIG. 2 is a schematic illustration of a portion of a binary mask layout.

Reference is next made to FIGS. 2 to 8 which schematically illustrate the process of the present invention as it is applied to the design and checking of a phase shifting mask layout according to one preferred embodiment of the present invention. FIG. 2 schematically represents a portion of a binary mask layout generally designated at 24 which includes two vertical lines 26 and 28 and one horizontal line 30.

Figure 3A:
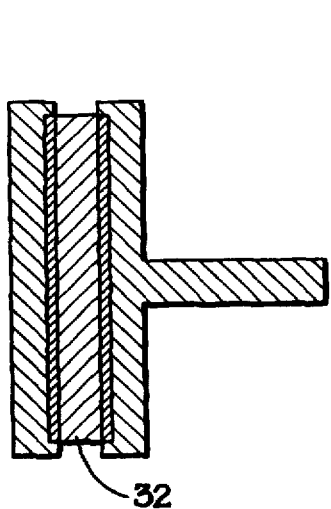
FIGS. 3A to 3C are schematic illustrations of a phase shifting mask design corresponding to the binary mask layout of FIG. 2.
Figure 3B:
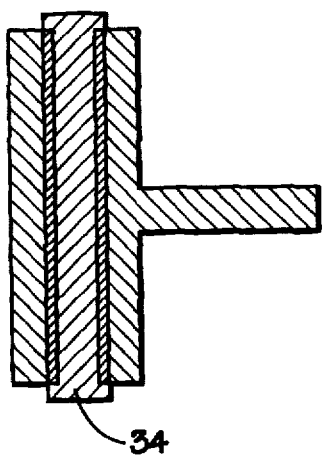
Figure 3C:
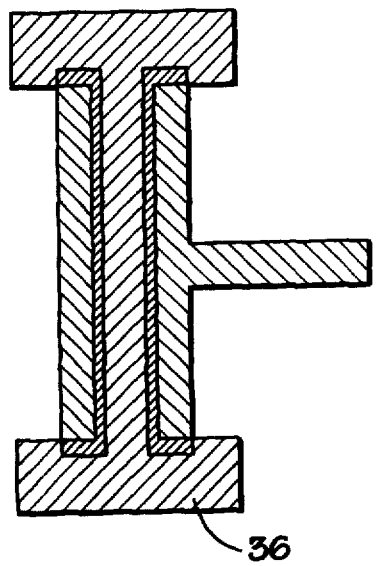

FIGS. 3A to 3C illustrate a phase shifting mask layout such as might be generated by design program 12 according to a preferred embodiment of the invention. Three phase shifting levels 32, 34 and 36 are designed so that the pattern can be printed utilizing a voting technique with each pattern representing a 60° etch. It will be appreciated by those skilled in the art that other phase shifting mask layout designs can also be generated and utilized according to the present invention.

Figure 4A:
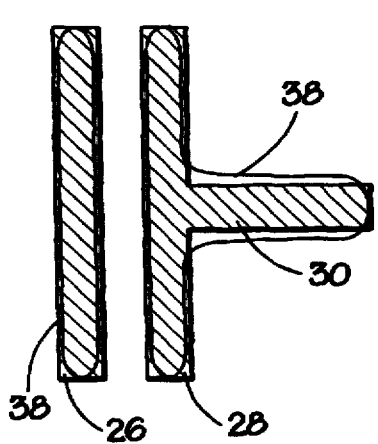
FIGS. 4A and 4B are schematic illustrations of simulated wafer images superimposed on the binary mask layout of FIG. 2.
Figure 4B:
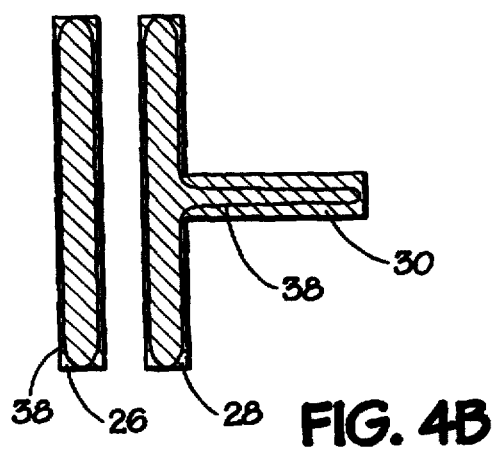

As illustrated in FIG. 1, the phase shifting mask layout of FIGS. 3A to 3C is processed through aerial image simulation software 16 to produce a simulated wafer image. In the preferred embodiment, the simulated wafer image is generated at both best focus and best focus ± a focus margin. FIG. 4A illustrates simulated wafer image 38 of the phase shifting mask layout of FIGS. 3A to 3C at best focus superimposed over the binary mask layout 24 of FIG. 2. FIG. 4B illustrates simulated wafer image 40 of the phase shifting mask layout of FIGS. 3A to 3C at best focus ± a focus margin superimposed over the binary mask layout 24 of FIG. 2. As can be seen in FIGS. 4A and 4B, there is a fairly close correlation between simulated wafer images 38 and 40 and vertical lines 26 and 28 of layout 24. However, there is a substantial variation between simulated wafer images 38 and 40 and horizontal line 30. When the comparison between the simulated wafer images 38 and 40 and binary mask layout 24 is performed by the data integrity verification and correction program, the program determines that the patterns do not correlate within the predetermined design rules. Accordingly, the patterns are fed back to the design program 12 for modification.

FIGS. 5A to 5C schematically illustrate a modified phase shifting design layout for generating the pattern of binary mask layout 24. Again, three phase shifting levels 42, 44 and 46 are generated so that the pattern can be formed using a voting technique.

The mask layout of FIGS. 5A to 5C is run through the aerial image simulation software 16 to generate simulated wafer images. FIG. 6A schematically illustrates the simulated wafer image 48 of the design of FIGS. 5A to 5C at best focus. FIG. 6B illustrates the simulated wafer image 50 at best focus ± a focus margin. As can be seen in FIGS. 6A and 6B, the simulated wafer images closely correlate with the vertical lines 26 and 28 of binary mask layout 24. However, while the simulated images of the horizontal line at both best focus and best focus ± a focus margin are similar, they are still slightly wider than horizontal line 30. As this data is run through the data integrity verification and correction program, it is checked to see whether it complies with the design rules. If it does not, the pattern is again sent back to the design program 12 to modify the mask layout. In the illustrated embodiment, because the only significant difference between the simulated images and the binary mask layout was in the width of the horizontal line, an easy method to correct this discrepancy is to change the line width of the horizontal line in the chrome image.

FIGS. 7A to 7C illustrate a modified mask layout for generating the binary mask layout design 24. FIGS. 7A to 7C are similar to FIGS. 5A to 5C except that the width of the horizontal line 52 in FIGS. 7A to 7C is slightly narrower than the width of the horizontal line 30 in FIGS. 5A to 5C. Additionally, the phase shifting levels 54 to 58 have been modified slightly to accommodate this change in line width.

FIG. 8 illustrates the simulated wafer image 60 of the design of FIGS. 7A to 7C superimposed on the binary mask layout 24 of FIG. 2. Both the simulated image at best focus and at best focus ± a focus margin are the same and correlate closely with the binary mask layout 24. Accordingly, the mask layout of FIGS. 7A to 7C is identified by the process as the final mask layout.

While the invention has been described with respect to the presently preferred embodiments, it will be appreciated by those skilled in the art that modifications and changes can be made to the process of the present invention without departing from its spirit or essential characteristics. For example, many different design programs can be utilized. Additionally, different design programs and techniques can be used to modify the mask layouts until the aerial image correlates within the design rules to the binary mask layout. Accordingly, all modifications or changes which come within the meaning and range of equivalency of the claims are to be embraced within their scope.

What is claimed is:

1. A process for checking a mask layout comprising:

obtaining a binary mask layout design;

generating a phase shifting mask layout having multiple layers that are printed using a voting technique to correspond to said binary mask layout design;

calculating an aerial image of said mask layout using simulation software; and comparing said aerial image to said binary mask layout design.

2. A process for checking a mask layout as defined in claim 1 wherein said aerial image is calculated and compared at both best focus and best focus ± a focus margin.

3. A process for checking a mask layout as defined in claim 1 wherein said aerial image is compared to said binary mask layout design using a design rule checker.

4. A process for checking a mask layout as defined in claim 1 further comprising generating a modified mask layout to correspond to said binary mask layout design if said comparison of said aerial image to said binary mask layout design does not fall with predetermined design rules.

5. A process for designing a mask layout comprising:

obtaining a binary mask layout design;

generating a phase shifting mask layout having multiple layers that are printed using a voting technique to correspond to said binary mask layout design;

calculating an aerial image of said mask layout using simulation software;

comparing said aerial image to said binary mask layout design using a design rule checker; and modifying said mask layout to more closely correspond to said binary mask layout design if said comparison of said aerial image to said binary mask layout design does not fall within predetermined design rules.

6. A process for designing a mask layout as defined in claim 5 wherein said aerial image is calculated and compared at both best focus and best focus ± a focus margin.

* * * * *